United States Patent [19]

Keville et al.

[11] Patent Number: 4,986,894
[45] Date of Patent: Jan. 22, 1991

[54] CATALYTIC HYDROISOMERIZATION PROCESS

[75] Inventors: Kathleen M. Keville, Woodbury; Quang N. Le, Cherry Hill; Wang-Tsee T. Mo, Mt. Laurel, all of N.J.; Mae K. Rubin, Bala Cynwyd, Pa.

[73] Assignee: Mobil Oil Corp., Fairfax, Va.

[21] Appl. No.: 495,545

[22] Filed: Mar. 19, 1990

Related U.S. Application Data

[63] Continuation-in-part of Ser. No. 254,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .............................................. C10G 47/20
[52] U.S. Cl. ........................................ 208/27; 208/18; 208/46; 208/111; 585/739
[58] Field of Search ................. 208/46, 111, 18, 27; 585/739

[56] References Cited

U.S. PATENT DOCUMENTS

| | | | |
|---|---|---|---|
| 3,894,938 | 7/1975 | Gorring et al. | 208/97 |
| 4,176,050 | 11/1979 | Chen et al. | 208/111 |
| 4,181,598 | 1/1980 | Gillespie et al. | 208/58 |
| 4,358,362 | 11/1982 | Smith et al. | 208/91 |
| 4,419,220 | 12/1983 | LaPierre et al. | 208/111 |
| 4,439,409 | 3/1984 | Puppe et al. | 423/328 |
| 4,601,993 | 7/1986 | Chu et al. | 502/66 |
| 4,734,539 | 3/1988 | Lawlor et al. | 585/739 |
| 4,826,667 | 5/1989 | Zones et al. | 423/277 |
| 4,855,530 | 8/1989 | LaPierre et al. | 208/138 |
| 4,877,581 | 10/1989 | Chen et al. | 585/739 |
| 4,919,788 | 4/1990 | Chen et al. | 208/111 |

FOREIGN PATENT DOCUMENTS

| | | | |
|---|---|---|---|
| 231860 | 12/1987 | European Pat. Off. | 423/329 |
| 293032 | 11/1988 | European Pat. Off. | 423/326 |

*Primary Examiner*—Anthony McFarlane
*Attorney, Agent, or Firm*—Alexander J. McKillop; Charles J. Speciale; Dennis P. Santini

[57] ABSTRACT

A process for dewaxing waxy hydrocarbon feedstocks to produce distillate fuels or lubricant stocks having improved pour point properties. The process comprises catalytic hydroisomerization of the feedstock over catalyst comprising a synthetic porous crystalline material characterized in its calcined form by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms, and an Alpha Value of 10 or less.

21 Claims, 2 Drawing Sheets

CATALYTIC HYDROISOMERIZATION PROCESS

CROSS-REFERENCE TO RELATED APPLICATION

This application is a continuation-in-part of U.S. patent application Ser. No. 254,524, filed Oct. 6, 1988, now U.S. Pat. No. 4,954,325, which is a continuation-in-part of U.S. patent application Ser. No. 98,176, filed Sept. 18, 1987, now abandoned, which is a continuation-in-part of U.S. patent application Ser. No. 890,268 filed July 29, 1986, now abandoned.

BACKGROUND OF THE INVENTION

1. Field of the Invention

This invention relates to a process for dewaxing hydrocarbon oils by a catalytic hydroisomerization process.

2. Background of the Art

Processes for dewaxing petroleum distillates have been known for a long time. Dewaxing is required when highly paraffinic oils are to be used in products which need to remain mobile at low temperatures e.g. lubricating oils, heating oils, jet fuels. The higher molecular weight straight chain normal and slightly branched paraffins which are present in oils of this kind are waxes which are the cause of high pour points in the oils and if adequately low pour points are to be obtained, these waxes must be wholly or partly removed. In the past, various solvent removal techniques were used e.g. propane dewaxing, MEK dewaxing, but the decrease in demand for petroleum waxes as such, together with the increased demand for gasoline and distillate fuels, has made it desirable to find processes which not only remove the waxy components but which also convert these components into other materials of higher value. Catalytic dewaxing processes achieve this end by selectively cracking the longer chain n-paraffins, to produce lower molecular weight products which may be removed by distillation. Processes of this kind are described, for example, in U.S. Pat. No. 3,668,113.

Zeolites, both natural and synthetic, crystalline materials (usually aluminosilicates), can be employed as catalysts for dewaxing, as well as for other processes. The feature which gives zeolite their special utility as catalysts is that they are porous microcrystalline structures. Pore size and shape determine the selectivity of a particular type of zeolite for particular reaction products. Catalytic behavior of a zeolite is also affected by the composition, i.e., its silica/alumina ratio. Zeolite are often used in conjunction with other materials, such as metals, e.g., platinum, nickel, molybdenum, tungsten and/or oxides, e.g., $Al_2O_3$, $SiO_2$.

The crystal structure of a zeolite may be determined by x-ray diffraction analysis, which gives a diffraction pattern unique to each type of zeolite.

In order to obtain the desired selectivity for dewaxing, the catalyst has usually been a zeolite having a pore size which admits the straight chain n-paraffins either alone or with only slightly branched chain paraffins, but which excludes more highly branched materials, cycloaliphatics and aromatics. Zeolites such as ZSM-5, ZSM-11, ZSM-12, ZSM-23, ZSM-35 and ZSM-38 have been proposed for this purpose in dewaxing processes and their use is described in U.S. Pat. Nos. 3,894,938; 4,176,050; 4,181,598; 4,222,855; 4,229,282 and 4,247,388. A dewaxing process employing synthetic offretite is described in U.S. Pat. No. 4,259,174. A hydrocracking process employing zeolite beta as the acidic component is described in U.S. Pat. No. 3,923,641.

Since dewaxing processes of this kind function by means of cracking reactions, a number of useful products become degraded to lower molecular weight materials. For example, olefins and naphthalenes may be cracked down to butane, propane, ethane and methane and so may the lighter n-paraffins which do not, in any event, contribute to the waxy nature of the oil. Because these lighter products are generally of lower value than the higher molecular weight materials, it would obviously be desirable to avoid or to limit the degree of cracking which takes place during a catalytic dewaxing process, but to this problem there has as yet been no solution.

Another unit process frequently encountered in petroleum refining is isomerization. In this process, as conventionally operated, low molecular weight $C_4$ to $C_6$ n-paraffins are converted to iso-paraffins in the presence of an acidic catalyst such as aluminum chloride or an acidic zeolite as described in G.B. No. 1,210,335. Isomerization processes for pentane and hexane which operate in the presence of hydrogen have also been proposed but since these processes operate at relatively high temperatures and pressures, the isomerization is accompanied by extensive cracking induced by the acidic catalyst, so that, once more, a substantial proportion of useful products is degraded to less valuable lighter fractions.

However, distillate feedstocks can be effectively dewaxed by isomerizing the waxy paraffins without substantial cracking if the isomerization is carried out over zeolite beta as a catalyst, especially if the catalyst includes a hydrogenation/dehydrogenation component such as platinum or palladium. The hydrogenation/dehydrogenation component may be used in the absence of added hydrogen to promote certain hydrogenation-dehydrogenation reactions which will take place during the isomerization.

The process is carried out at elevated temperature and pressure. Temperatures will normally be from 250° C. to 500° C. (about 480° F. to 930° F.) and pressures from atmospheric up to 25,000 kPa (3,600 psig). Space velocities will normally be from 0.1 to 20. A description of such a process may be found in U.S. Pat. No. 4,419,220, herein incorporated by reference in its entirety.

U.S. Pat. No. 4,601,933 discloses a process for dewaxing lubricating oil feedstocks by passing a waxy feedstock over a catalyst bed containing a mixture of a medium pore zeolite and a large pore zeolite having isomerization activity.

Further information about catalytic dewaxing may be found in U.S. Pat. Nos. 3,894,938; 4,176,050; 4,358,362; and 4,181,598.

SUMMARY OF THE INVENTION

It has now been found that dewaxing of hydrocarbon oils can be achieved more effectively by catalytic isomerization over catalyst comprising synthetic crystalline material characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms. The isomerization may be conducted either in the presence or absence of added hydrogen. The preferred form of the catalyst contains boron and it should include a hydrogenation component such as platinum or palladium in order to promote the reactions which occur. The hydrogenation component may be used in the absence of added hydrogen to promote certain hydrogenation-dehydrogenation reactions which will take place during the isomerization.

The process is carried out at elevated temperature and pressure. Temperatures will normally be from about 480° F. to about 930° F., preferably from about 650° F. to about 800° F. and pressures from atmospheric up to about 25,000 kPa (3,600 psig), preferably from about 200 psig to about 1200 psig. Space velocities will normally be from 0.1 to 20 hr$^{-1}$.

The enhanced selectivity of the catalyst for hydroisomerization is beneficial to the production of distillate fuels, and high VI (viscosity index), low pour point lube base stock. Additional advantages may be gained by reduced coking tendency and prolonged catalyst life.

DESCRIPTION OF THE PREFERRED EMBODIMENTS

Figure 1:
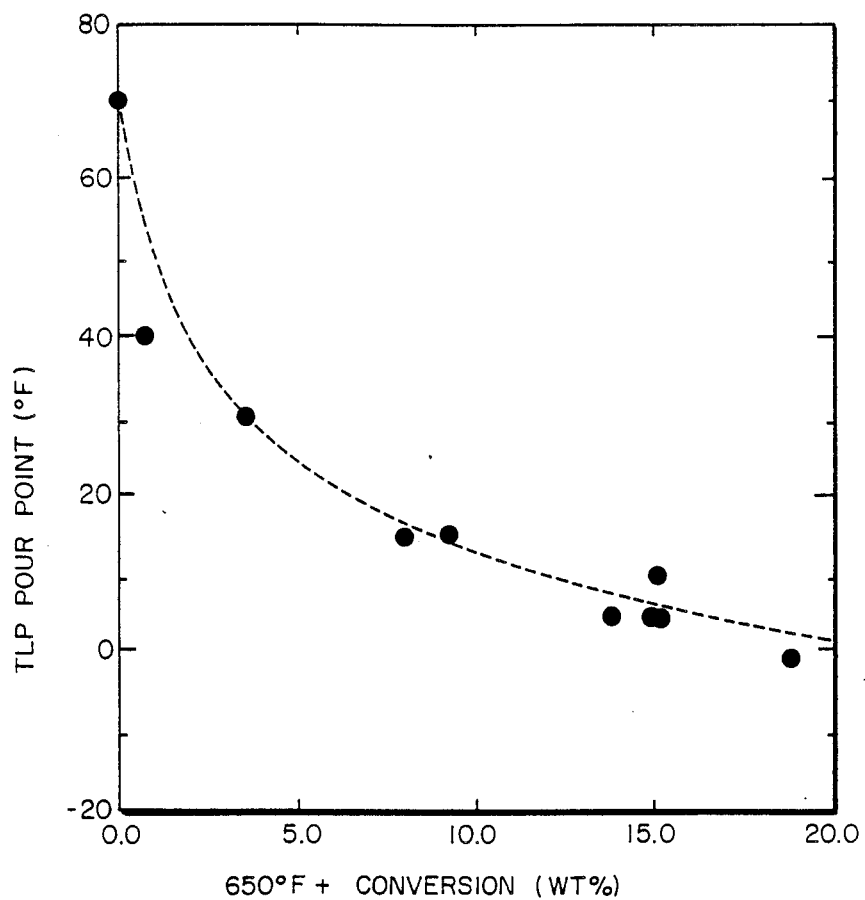
FIGS. 1 and 2 graphically illustrate the pour point reduction of feedstock hydroisomerized by the process of the present invention for Arab Light LVGO and Chiba MPHC Bottoms, respectively.

The entire contents of applications Ser. Nos. 254,524; 98,176 and 890,268 are incorporated herein by reference.

Feedstock

The present process may be used to dewax a variety of feedstocks ranging from relatively light distillate fractions up to high boiling stocks such as whole crude petroleum, reduced crudes, vacuum tower residua, cycle oils, FCC tower bottoms, gas oils, vaccum gas oils, deasphalted residua and other heavy oils. The feedstock will normally be a C$_{10}$+ feedstock since lighter oils will usually be free of significant quantities of waxy components. However, the process is particularly useful with waxy distillate stocks such as gas oils, kerosenes, jet fuels, lubricating oil stocks, heating oils and other distillate fractions whose pour point and viscosity need to be maintained within certain specification limits. Lubricating oil stocks will generally boil above 230° C. (450° F.), more usually above 315° C. (600° F.). Hydrocracked stocks are a convenient source of stocks of this kind and also of other distillate fractions since they normally contain significant amounts of waxy n-paraffins which have been produced by the removal of polycyclic aromatics. The feedstock for the present process will normally be a C$_{10}$+ feedstock containing paraffins, olefins, naphtenes, aromatics and heterocyclic compounds and with a substantial proportion of higher molecular weight n-paraffins and slightly branched paraffins which contribute to the waxy nature of the feedstock. During the processing, the n-paraffins become isomerized to iso-paraffins and the slightly branched paraffins undergo isomerization to more highly branched aliphatics. At the same time, a measure of cracking does take place so that not only is the pour point reduced by reason of the isomerization of n-paraffins to the less waxy branched chain iso-paraffins but, in addition, the heavy ends undergo some cracking or hydrocracking to form liquid range materials which contribute to a low viscosity product. The degree of cracking which occurs is, however, limited so that the gas yield is reduced, thereby preserving the economic value of the feedstock.

Typical feedstocks include light gas oils, heavy gas oils and reduced crudes boiling above 150° C.

It is a particular advantage of the present process that the isomerization proceeds readily, even in the presence of significant proportions of aromatics may be successfully dewaxed. The aromatic content of the feedstock will depend, of course, upon the nature of the crude employed and upon any preceding processing steps such as hydrocracking which may have acted to alter the original proportion of aromatics in the oil. The aromatic content will normally not exceed 50 percent by weight of the feedstock and more usually will be not more than 10 to 30 percent by weight, with the remainder consisting of paraffins, olefins, naphthenes and heterocyclics. The paraffins content (normal and iso-paraffins) will generally be at least 20 percent by weight, more usually at least 50 to 60 percent by weight. Certain feedstocks such as jet fuel stocks may contain as little as 5 percent paraffins.

Catalyst

In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, I/I$_o$ × 100 |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | M-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, I/I$_o$ × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplanar d-Spacing (A) | Relative Intensity, I/I$_o$ × 100 |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |

TABLE C-continued

| Interplanar d-Spacing (A) | Relative Intensity, $I/I_o \times 100$ |
|---|---|
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

More specifically, it may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

W=0-20
M=20-40
S=40-60
VS=60-100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g., silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

The zeolite catalyst component for use herein has an Alpha Value of 10 or less, usually 5 or less.

Zeolite MCM-22 has a composition involving the molar relationship:

$$X_2O_3:(n)YO_2,$$

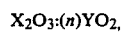

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

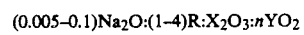

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Preferred metal ions include rare earth metals and metals of Groups IIA, IIIA, IVA, IB, IIB, IIIB, IVB and VIII of the Periodic Table of the Elements, and particularly a platinum type noble metal selected from platinum, palladium, ruthenium, rhodium, osmium or iridium.

In its calcined form, zeolite MCM-22 appears to be made up of a single crystal phase with little or no detectable impurity crystal phases and has an X-ray diffraction pattern including the lines listed in above Tables A-D.

Prior to its use in the catalyst composition herein, the synthetic porous crystalline material zeolite should be subjected to thermal treatment to remove part or all of any organic constituent present therein.

The zeolite present in the catalyst composition herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the zeolite and/or matrix with which the zeolite may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing the platinum metal-containing ion. Thus, suitable platinum compounds for this purpose include chloroplatinic acid, platinous chloride and various compounds containing the platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmosphere pressure can be employed for the thermal treatment, atmospheric pressure is preferred simply for reasons of convenience. The thermal temperature can be performed at a temperature of up to about 925° C.

Prior to its use in the catalyst composition and process of this invention, the zeolite crystals should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the crystalline material in a vacuum but a longer time will be required to achieve a suitable degree of dehydration.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, or organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30. wt.% solid $YO_2$. Where YO is silica, the use of a silica source containing at least about 30 wt.% solid silica, e.g., Ultrasil (a precipitated, spray dried silica containing about 90 wt.% silica) or HiSil (a precipitated hydrated $SiO_2$ containing about 87 wt.% silica, about 6 wt.% free $H_2O$ and about 4.5 wt.% bound $H_2O$ of hydration and having a particle size of about 0.02 micron) favors MCM-22 crystal formation from the above mixture and is a distinct difference over the synthesis method disclosed in U.S. Pat. No. 4,439,409. If another source of oxide of silicon, e.g., Q-Brand (a sodium silicate comprised of about 28.8 wt.% of $SiO_2$, 8.9 wt.% $Na_2O$ and 62.3 wt.% $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt.% solid $YO_2$, e.g., silica, and more preferably at least about 40 wt.% solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 material will vary with the nature of the reaction mixture employed and the crystallization conditions. In all cases, synthesis of the MCM-22 crystals is facilitated by the presence of at least about 0.01 percent, preferably about 0.10 percent and still more preferably about 1 percent, seed crystals based on the total weight of the crystalline product formed.

The zeolite crystals can be shaped into a wide variety of particule sizes. Generally speaking, the particules can be provided in the form of a powder, a granule or a molded product such as an extrudate having a particle size sufficient to pass through a 2 mesh (Tyler) screen and be substantially retained on a 400 mesh (Tyler) screen). In cases where the catalyst is molded, such as by extrusion, the crystals can be extruded before drying or partially dried and then extruded.

It may be desirable to incorporate the zeolite crystalline material with another material, i.e., a binder, which is resistant to the temperatures and other conditions employed in the process of this invention. Suitable binder materials include active and inactive materials and synthetic or naturally occurring zeolite as well as inorganic materials such as clays, silica and/or metal oxides such as alumina. The latter can be either naturally occurring or provided in the form of gelatinous precipitates or gels including mixtures of silica and metal oxides. Use of a binder material in conjunction with the zeolite, i.e., combined therewith or present during its synthesis, which itself is catalytically active may change the conversion and/or selectivity of the catalyst. Inactive materials suitable serve as diluents to control the amount of conversion so that products can be obtained economically and in a controlled fashion without having to employ other means for controlling the rate of reaction.

These materials can be incorporated into naturally occurring clays, e.g., bentonite and kaolin, to improve the crush strength of the zeolite under commercial operating conditions. Good crush strength is an advantageous attribute for commercial use since it prevents or delays breaking down of the catalyst into powder-like materials.

Naturally occurring clays which can be composited with the zeolite crystals include the montmorillonite and kaolin family, which families include the subbentonites, and the kaolines commonly known as Dixie, McNamee, Georgia and Florida clays or others in which the main mineral constituent is halloysite, kaolinite, dickite, nacrite, or anauxite. Such clays can be used in the raw state as originally minced or initially subjected to calcination, acid treatment or chemical modification. Binders useful for compositing with the zeolite also include inorganic oxides, notably alumina.

Apart from or in addition to the foregoing binder materials, the zeolite crystals can be composited with an organic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may also be advantageous to provide at least a part of the foregoing matrix materials in colloidal form so as to facilitate extrusion of the bound catalyst component(s).

The relative proportions of finely divided crystalline material and inorganic oxide matrix can vary widely with the zeolite content ranging from about 1 to about 95 percent by weight and more usually, particularly when the composite is prepared in the form of beads, in the range of about 2 to about 80 weight percent of the composite.

The stability of the zeolite catalyst may be increased by steaming, with suitable steam stabilization conditions including contacting the catalyst with, for example, 5-100% steam at a temperature of at least 300° C. (e.g. 300°-650° C.) for at least one hour (e.g. 1-200 hours) at a pressure of 100-2,500 kPa. In a more particular embodiment, the catalyst can be made to undergo steaming with 75-100% steam at 315°-500° C. and atmospheric pressure for 2-25 hours.

The preferred form of the zeolite for use in the present invention is a boron-containing MCM-22 prepared with a noble metal component such as platinum or palladium. The catalyst has a low acidity due to the incorporation of boron into the zeolite framework, and hence reduced hydrocracking activity. Selectivity and activity for hydroisomerization are excellent; distillate and/or lube yield are enhanced whereas light gas and naphtha production are reduced. Additional advantages may be gained by reduced coking tendency and prolonged catalyst life.

In order to more fully illustrate the process of this invention and the manner of practicing same, the following examples are presented. In examples which are illustrative of the synthesis of zeolite, whenever sorption data are set forth for comparision of sorptive capacities for water, cyclohexane and/or n-hexane, then were Equilibrium Absorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressure less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt.% for water vapor, greater than about 4.5 wt.%, usually greater than about 7 wt.% cyclohexane vapor and greater than about 10 wt.% for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078; in the *Journal of Catalysis*, vol. 4, p. 527 (1965); vol. 6, p. 278 (1966); and vol. 61, p. 395 (1980), each incorporated herein by reference as to that description. The experimental conditions of the test used herein include a constant temperature of 538° C. and a variable flow rate as described in detail in the *Journal of Catalysis*, vol. 61, p. 395. The Alpha Value of the synthetic zeolite catalyst component for use in this invention is 10 or less, usually 5 or less.

EXAMPLE 1

One part sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (90% $SiO_2$).

The reaction mixture had the following composition, in mole ratios:

| | |
|---|---|
| $SiO_2/Al_2O_3$ | = 30.0 |
| $OH^-/SiO_2$ | = 0.18 |
| $H_2O/SiO_2$ | = 44.9 |
| $Na/SiO_2$ | = 0.18 |
| $R/SiO_2$ | = 0.35 | where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the zeolite was measured to be 494 $m^2/g$.

The chemical composition of the uncalcined material was determined to be as follows:

| Component | wt. % |
|---|---|
| SiO$_2$ | 66.9 |
| Al$_2$O$_3$ | 5.40 |
| Na | 0.03 |
| N | 2.27 |
| Ash | 76.3 |
| SiO$_2$O/Al$_2$O$_3$, mole ratio | 21.10 |

TABLE E

| Degrees 2-Theta | Interplanar d-Spacing (A) | I/I$^o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surfaces area measurements were of the calcined product.

TABLE F

| Example | 3 | 4 | 5 |
|---|---|---|---|
| Synthesis Mixture, mole ratios | | | |
| SiO$_2$/Al$_2$O$_3$ | 30.0 | 30.0 | 30.0 |
| OH$^-$/SiO$_2$ | 0.18 | 0.18 | 0.18 |
| H$_2$O/SiO$_2$ | 19.4 | 19.4 | 44.9 |
| Na/SiO$_2$ | 0.18 | 0.18 | 0.18 |
| R/SiO$_2$ | 0.35 | 0.35 | 0.35 |
| Product Composition, Wt. % | | | |

TABLE F-continued

| Example | 3 | 4 | 5 |
|---|---|---|---|
| SiO$_2$ | 64.3 | 68.5 | 74.5 |
| Al$_2$O$_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| SiO$_2$O/Al$_2$O$_3$, mole ratio | 22.5 | 20.9 | 26.0 |
| Adsorption, Wt. % | | | |
| H$_2$O | 14.9 | 13.6 | 14.6 |
| Cyclohexane | 12.5 | 12.2 | 13.6 |
| n-Hexane | 14.6 | 16.2 | 19.0 |
| Surface Area, m$^2$/g | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of of 50% NaOH solution and 44.19 parts of H$_2$O. To the combined solution was added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table G:

TABLE G

| Product Composition (uncalcined) | |
|---|---|
| C | 12.1 wt. % |
| N | 1.98 wt. % |
| Na | 640 ppm |
| Al$_2$O$_3$ | 5.0 wt. % |
| SiO$_2$ | 74.9 wt. % |
| SiO$_2$/Al$_2$O$_3$, mole ratio | 25.4 |
| Adsorption, wt. % | |
| Cyclohexane | 9.1 |
| N-Hexane | 14.9 |
| H$_2$O | 16.8 |
| Surface Area, m$^2$/g | 479 |

EXAMPLE 8

Twenty-five grams of solid crystal product from Example 7 were calcined in a flowing nitrogen atmospheres at 538° C. for 5 hours, followed by purging with 5% oxygen gas (balance N$_2$) for another 16 hours at 538° C.

Individual 3g samples of the calcined material ion-exchanged 100 ml of 0.1N TEABr, TPABr and LaCl$_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| | Exchange Ions | | |
|---|---|---|---|
| Ionic Composition, wt. % | TEA | TPA | La |
| Na | 0.095 | 0.089 | 0.063 |
| N | 0.30 | 0.38 | 0.03 |
| C | 2.89 | 3.63 | — |

| Exchange Ions | | | |
|---|---|---|---|
| Ionic Composition, wt. % | TEA | TPA | La |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | |
|---|---|
| $SiO_2/B_2O_3$ | = 6.1 |
| $OH^-/SiO_2$ | = 0.06 |
| $H_2O/SiO_2$ | = 19.0 |
| $K/SiO_2$ | = 0.06 |
| $R/SiO_2$ | = 0.30 | where R is hexamethyleneimine.

The mixture was crystallized in a stainless steel reaction, with agitation, at 150° C. for 8 days. The crystalline product was filtered, washed with water and dried at 120° C. A portion of the product was calcined for 6 hours at 240° C. and found to have the following sorption capacities:

| | |
|---|---|
| $H_2O$ | 11.7 wt. % |
| Cyclohexane | 7.5 wt. % |
| n-Hexane | 11.4 wt. % |

The surface area of the calcined crystalline material was measured (BET) to be 405 $m^2/g$.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio | 1406 |
| $SiO_2/Al + B)_2O_3$, molar ratio | 25.8 |

EXAMPLE 12

A portion of the calcined crystalline product of Example 11 was treated with $NH_4Cl$ and again calcined. The final crystalline product was tested in the Alpha test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | |
|---|---|
| $SiO_2/B_2O_3$ | = 12.3 |
| $OH^-/SiO_2$ | = 0.056 |
| $H_2O/SiO_2$ | = 18.6 |
| $K/SiO_2$ | = 0.056 |
| $R/SiO_2$ | = 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ | 14.4 wt. % |
| Cyclohexane | 4.6 wt. % |
| n-Hexane | 14.0 wt. % |

The surface area of the calcined crystalline material was measured to be 438$m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al + B)_2O_3$, molar ratio | 28.2 |

EXAMPLE 14

A portion of the calcined crystalline product of Example 13 was tested in the Alpha Test and found to have an Alpha Value of 5.

EXAMPLE 15

A boron-containing zeolite MCM-22 was prepared in accordance with Example 13 wherein a portion of the aluminum is substituted with boron. The as-synthesized zeolite was combined with a silica binder and converted to the hydrogen form. The silica-bound boron-containing MCM-22 was then exchanged for 4 hours with $Pt(NH_3)_4Cl_2$ to replace at least some cations with platinum, and calcined in air at 660° F. for 3 hours. The finished catalyst comprised 65 wt.% zeolite supported on silica. The zeolite had the following properties:

| | |
|---|---|
| Alpha (prior to Pt exchange) | 2 |
| SiO$_2$/Al$_2$O$_3$ (molar ratio) | 1060 |
| Boron content | 0.92 wt. % |
| Platinum content | 0.7 wt. % |

EXAMPLE 16

A hydrotreated Arab Light LVGO (Light Virgin Gas Oil) feed was dewaxed under hydroisomerization condition using the catalyst of Example 15. The feed had a nitrogen level of 66 ppm, API gravity of 29.6 and a pour point of 70° F. Hydroisomerization was conducted in a fixed bed reaction in a series of runs between 650° F. and 765° F. and at 400 psig hydrogen. Pour point of the total liquid product (TLP), indicative of the hydroisomerization reaction, as a function of the 650° F.+ fraction boiling point conversion, a measurement of hydrocracking activity, is plotted in FIG. 1.

The data indicated that the Pt/B-MCM-22 catalyst had a very good dewaxing selectivity. The pour point of the feed was reduced by at least 50° with less than 10 wt.% 650° F.+ conversion. This confirmed the dewaxing activity and superior selectivity of the catalyst in this process.

EXAMPLE 17

Figure 2:
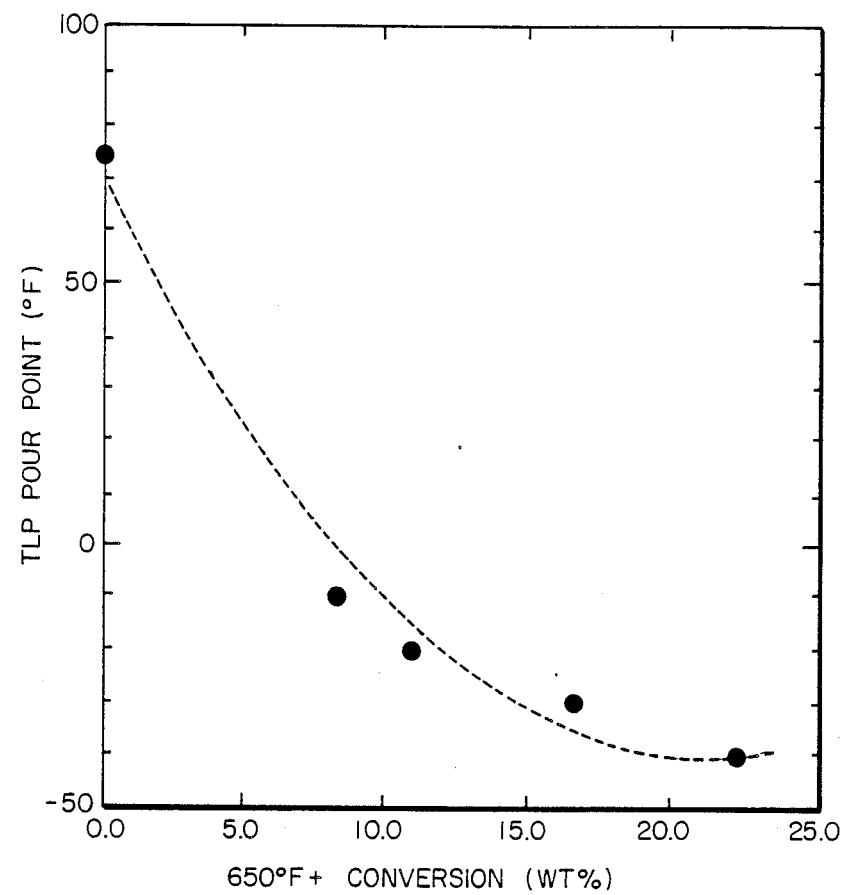

A MPHC (Moderate Pressure Hydrocracking) bottom having 42 ppm nitrogen, and 75° F. pour point was dewaxed under hydroisomerization conditions using the catalyst of Example 15. Hydroisomerization was conducted in a fixed bed reaction in a series of runs between 730° F. and 780° F. at 400 psig hydrogen. Some data are shown in Table H below. Total liquid product (TLP) pour point as a function of the 650° F.+ conversion wt.% is plotted in FIG. 2

TABLE H

| | Feed | Run 1 | Run 2 | Run 3 | Run 4 |
|---|---|---|---|---|---|
| Temperature, °F. | — | 730 | 750 | 770 | 780 |
| H$_2$ Pressure, psig | — | 400 | 400 | 400 | 400 |
| 650° F.+ Conversion, wt. % | — | 8.4 | 10.9 | 16.7 | 22.5 |
| Product Yields/Properties: | | | | | |
| C$_1$–C$_4$, wt % | — | 0.6 | 1.0 | 1.5 | 2.1 |
| C$_5$–330° F. Naphtha, wt. % | — | 2.5 | 3.6 | 6.9 | 8.2 |
| 330–650° F. Dist., wt. % | 7.0 | 11.8 | 12.5 | 14.2 | 17.6 |
| TLP Pour Point, °F. | 75 | −10 | −25 | −40 | −45 |

As can be seen from Table H a dramatic reduction in pour point can be achieved on a waxy feedstock in the present process.

EXAMPLE 18

In this example, the catalyst of Example 15 was evaluated at two different hydrogen partial pressures, 400 psig and 800 psig, with a MPHC bottom. The results are shown in Table I.

TABLE I

| | Feed | Run 1 | Run 2 | Run 3 | Run 4 |
|---|---|---|---|---|---|
| Temperature, °F. | — | 730 | 780 | 730 | 780 |
| H$_2$ Pressure, psig | — | 400 | 400 | 800 | 800 |
| 650° F.+ Conversion, wt. % | — | 8.4 | 22.5 | 3.3 | 17.1 |
| Product Yields/Properties: | | | | | |
| C$_1$–C$_4$, wt. % | — | 0.6 | 2.1 | 0.3 | 1.3 |
| C$_5$–330° F. Naphtha, wt. % | — | 2.5 | 8.2 | 1.1 | 6.5 |
| 330–650° F. Dist., wt. % | 7.0 | 11.8 | 17.6 | 8.9 | 15.2 |
| TLP Pour Point, °F. | 75 | −10 | −45 | 15 | −15 |

The results indicated that hydrocracking reaction was further suppressed under the 800 psig condition, while the dewaxing through isomerization remains very effective. This example demonstrates the capability of the catalyst as a very effective hydroisomerization catalyst, and the potential for controlling the isomerization selectivity by varying operating conditions.

The above examples indicate that the boron-containing zeolite for use herein exhibits high selectivity for hydroisomerization reactions and reduced hydrocracking activity. The relatively increased hydroisomerization selectivity and product yield, as demonstrated by this catalyst, can be used to produce low pour point, high VI, lube base stocks, as well as dewaxed distillate fuels.

What is claimed is:

1. A process for dewaxing a waxy hydrocarbon feedstock, said process comprising contacting said feedstock with a catalyst composition under hydroisomerization conditions to produce a product with a reduced pour point, said catalyst composition comprising a synthetic zeolite characterized by an X-ray diffraction pattern including values substantially as shown in Table A of the specification and having an Alpha Value of about 10 or less.

2. The process of claim 1 wherein said zeolite is characterized by an X-ray diffraction pattern including values substantially as shown in Table B of the specification.

3. The process of claim 1 wherein the zeolite is characterized by an x-ray diffraction pattern including values substantially as shown in Table C of the specification.

4. The process of claim 1 wherein the zeolite is characterized by an X-ray diffraction pattern including values significantly as shown in Table D of the specification.

5. The process of claim 1 wherein the synthetic zeolite has a composition comprising the molar relationship:

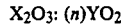

$$X_2O_3 : (n)YO_2$$

wherein X is a trivalent element selected from the group consisting of aluminum, boron, iron, and gallium, Y is a tetravalent element selected from the group consisting of silicon and germanium, and n is at least about 10.

6. The process of claim 1 wherein said synthetic zeolite has been treated to replace original ions, at least in part, with an ion or mixture of ions selected from the group consisting of hydrogen, rare earth metals, and metals of Groups IIA, IIIA, IVA, IB, IIB, IIIB, IVB, VIB and VIII of the Periodic Table.

7. The process of claim 1 wherein said synthetic zeolite has been thermally treated at a temperature of up to about 925° C.

8. The process of claim 1 wherein the waxy hydrocarbon feedstock contains paraffins.

9. The process of claim 1 wherein the waxy hydrocarbon feedstock is selected from the group consisting of whole crude petroleum, gas oil, cycle oil, catalytic cracker tower bottoms, and a heavy oil fraction having an initial boiling point of 450° F. or higher.

10. The process of claim 1 wherein the hydroisomerization conditions include a temperature of from about 480° F. to 930° F., a pressure of from atmospheric to 3,600 psig, and a liquid hourly space velocity of from about 0.1 to about 20 hr$^{-1}$.

11. The process of claim 5 wherein X comprises boron.

12. The process of claim 1 wherein the synthetic zeolite has an Alpha Value of about 5 or less.

13. The process of claim 1 wherein said catalyst composition comprises a binder selected from the group consisting of silica, magnesia, zirconia, thoria, beryllia, titania and mixtures thereof.

14. The process of claim 1 wherein said catalyst comprises one or more noble metals.

15. The process of claim 14 wherein said noble metals are selected from the group consisting of platinum and palladium.

16. The process of claim 1 wherein said waxy hydrocarbon feedstock is dewaxed in the presence of hydrogen.

17. The process of claim 1 wherein the hydrocarbon feedstock is a vaccum tower residua, deasphalted residua or a vacuum gas oil.

18. A process for improving lubricant properties of a waxy hydrocarbon feedstock, said process comprising contacting said feedstock with a catalyst composition in the presence of hydrogen under hydroisomerization conditions, said catalyst composition comprising a synthetic zeolite containing boron, having an Alpha Value of 10 or less, and an X-ray diffraction pattern including values substantially as set forth in Table A of the specification, said catalyst having been treated to contain a noble metal selected from the group consisting of platinum and palladium, wherein the hydroisomerization conditions include a temperature of from about 650° F. to about 800° F. and a pressure of about 200 to about 1200 psig.

19. The process of claim 18 wherein said hydroisomerization conditions include a temperature of from about 650° F. to about 765° F.

20. The process of claim 18 wherein said hydroisomerization conditions include a temperature of from about 730° F. to about 780° F. and a pressure of from about 400 psig to about 800 psig.

21. The process of claim 18 wherein said catalyst composition comprises a binder selected from the group consisting of silica, magnesia, zirconia, thoria, beryllia, titania and mixtures thereof.

* * * * *